(12) United States Patent
Seong et al.

(10) Patent No.: US 7,285,528 B2
(45) Date of Patent: Oct. 23, 2007

(54) AGONISTS AND ANTAGONISTS OF GONADOTROPIN-RELEASING HORMONE-2, AND USE THEREOF

(75) Inventors: Jae-Young Seong, Gwangju (KR); Hyuk-Bang Kwon, Seoul (KR)

(73) Assignee: Neurogenex Co., Ltd., Seoul (KR)

( * ) Notice: Subject to any disclaimer, the term of this patent is extended or adjusted under 35 U.S.C. 154(b) by 0 days.

(21) Appl. No.: 10/513,083

(22) PCT Filed: Mar. 24, 2003

(86) PCT No.: PCT/KR03/00572

§ 371 (c)(1), (2), (4) Date: Nov. 22, 2005

(87) PCT Pub. No.: WO03/093304

PCT Pub. Date: Nov. 13, 2003

(65) Prior Publication Data

US 2006/0135432 A1 Jun. 22, 2006

(30) Foreign Application Priority Data

May 3, 2002 (KR) .................. 10-2002-0024423

(51) Int. Cl.
*A61K 38/08* (2006.01)
(52) U.S. Cl. ............................................ 514/2
(58) Field of Classification Search .............. None
See application file for complete search history.

(56) References Cited

OTHER PUBLICATIONS

White et al., "Second gene for gonadotropin-releasing hormone in humans." PNAS, 1998, 95, 305-9.*
Neill et al., "A gonadotropin-releasing hormone (GnRH) receptor specific for GnRH II in primates." Biochem. Biophys. Res. Com., 2001, 282, 1012-8.*
Lescheid et al., "A second form of gonadotropin-releasing hormone (GnRH) with characteristics of chicken GnRH-II is present in the primate brain." Endo., 1997, 138, 5618-29.*
Kang et al., "Differential regulation of two forms of gonadotropin-releasing hormone messenger ribonucleic acid in human granulosa-luteal cells." Endo., 2001, 142, 182-92.*
Wang et al., "Preferential ligand selectivity of the monkey type-II gonadotropin-releasing hormone (GnRH) receptor for GnRH-2 and its analogs." Mol. Cell Endo., 2003, 209, 33-42.*
Maiti et al., "GnRH-II analogs for selective activation and inhibition of non-mammalian and type-II mammalian GnRH receptors." Mol. Cells, 2003, 16, 173-9.*
Chou et al. "Differential effects of gonadotropin-releasing hormone I and II on the urokinase-type plasminogen activator/plasminogen activator inhibitor system in human decidual stromal cells in vitro." J. Clin. End. Met., 2002,87,5594-603.*
Emons et al. "GnRH antagonists in the treatment of gynecological and breast cancers." Endo.-Rel. Canc., 2003, 10, 291-9.*
Grundker et al., "Biology of the gonadotropin-releasing hormone system in gynecological cancers." Eur. J. Endo., 2002, 146, 1-14.*
Ginalski et al. "Practical lessons from protein structure prediction." Nuc. Ac. Res., 2005, 33, 1874-1891.*
Rudinger "Characteristic of the amino acids as components of a peptide hormone sequence." (Peptide Hormones (Ed. J.A. Parson). University Park Press. Baltimore, 1976, pp. 1-7.*
Pitt et al. "Single amino acid substitution mutants of Klebsiella pneumoniae singma54 defective in transcription" Nuc. Ac. Res., 2000, 28, 4419-4427.*
Bradley et al. "Limits of Cooperativity in a Structurally Modular Protein: Response of the Notch Ankyrin Domain to Analogous Alanine Substitutions in Each Repeat" J. Mol. Biol., 2002, 324, 373-386.*
Flanagan et al. "Truncated staphyloccal nuclease in compact but disordered" Proc. Natl. Acad. Sci. USA, 1992, 89, 748-752.*
Sawai et al. "Impact of single-residue mutations on the structure and function of ovispirin/novispirin antimicrobial peptides" Prot. Engin., 2002, 15, 225-232.*
Schnog et al. "Sickle cell disease; a general overview" J. Med., 2004, 62, 364-374.*

* cited by examiner

*Primary Examiner*—Cecilia J. Tsang
*Assistant Examiner*—Christina M. Bradley
(74) *Attorney, Agent, or Firm*—Jones Day

(57) ABSTRACT

The present invention relates to agonists and antagonists of gonadotropin-releasing hormone-2 (GnRH-2), which regulates the activity of GnRH-2 by specifically binding to GnRH-2 receptors, and uses thereof The pharmaceutical compositions comprising the GnRH-2 agonists and antagonists according to the present invention are useful for the treatment of reproductive physiology diseases and steroid-related cancer cells because they specifically bind to the GnRH-2 receptors, and they are also usefully applicable to the raising industry of non-mammalian animals, i.e., birds and fish.

3 Claims, 9 Drawing Sheets

Fig. 1

| | | |
|---|---|---|
| GnRH-1 | pyro-Glu-His-Trp-Ser-Tyr-Gly-Leu-Arg-Pro-GlyNH$_2$ | (SEQ ID NO:13) |
| GnRH-2 | pyro-Glu-His-Trp-Ser-His-Gly-Trp-Tyr-Pro-GlyNH$_2$ | (SEQ ID NO:1) |
| GnRH-2 agonist | pyro-Glu-His-Trp-Ser-Xaa$_5$-Xaa$_6$-Xaa$_7$-Xaa$_8$-Pro-GlyNH$_2$ | (SEQ ID NO:2) |
| [D-Ala6]GnRH-2 | pyro-Glu-His-Trp-Ser-His-*D-Ala*-Trp-Tyr-Pro-GlyNH$_2$ | (SEQ ID NO:3) |
| [D-Lys6]GnRH-2: | pyroGlu-His-Trp-Ser-His-*D-Lys*-Trp-Tyr-Pro-GlyNH$_2$ | (SEQ ID NO:4) |
| [D-Ala6, Leu7]GnRH-2: | pyroGlu-His-Trp-Ser-His-*D-Ala-Leu*-Tyr-Pro-GlyNH$_2$ | (SEQ ID NO:5) |
| [Leu5, D-Ala6]GnRH-2: | pyroGlu-His-Trp-Ser-*Leu-D-Ala*-Trp-Tyr-Pro-GlyNH$_2$ | (SEQ ID NO:6) |
| [Tyr5,D-Ala6,Leu8]GnRH-2: | pyroGlu-His-Trp-Ser-*Tyr-D-Ala*-Trp-*Leu*-Pro-GlyNH$_2$ | (SEQ ID NO:7) |
| [D-Ala6, Tyr7, Trp8]GnRH-2: | pyroGlu-His-Trp-Ser-His-*D-Ala-Tyr-Trp*-Pro-GlyNH$_2$ | (SEQ ID NO:8) |
| GnRH-2 antagonist: | Ac-D-2Nal-(A)-D-Phe-D-3Pal-Ser-Xaa$_5$-D-Cit-Trp-Xaa$_8$-Pro-D-AlaNH$_2$ | (SEQ ID NO:9) |
| Trptorelix-1: | Ac-D-2Nal-(4Cl)-D-Phe-D-3Pal-Ser-Tyr-D-Cit-Trp-Tyr-Pro-D-AlaNH$_2$ | (SEQ ID NO:10) |
| Trptorelix-2: | Ac-D-2Nal-(4Cl)-D-Phe-D-3Pal-Ser-*His*-D-Cit-Trp-Tyr-Pro-D-AlaNH$_2$ | (SEQ ID NO:11) |
| Trptorelix-3: | Ac-D-2Nal-(4Cl)-D-Phe-D-3Pal-Ser-Tyr-D-Cit-Trp-*Leu*-Pro-D-AlaNH$_2$ | (SEQ ID NO:12) |
| Cetrorelix: | Ac-D-2Nal-(4Cl)-D-Phe-D-3Pal-Ser-Tyr-D-Cit-Leu-Arg-Pro-D-AlaNH$_2$ | (SEQ ID NO:15) | bfGnRHR-1 bfGnRHR-2 bfGnRHR-3

Rat GnRHR bfGnRHR-2 bfGnRHR-3

SEQUENCE LISTING

```
<160> NUMBER OF SEQ ID NOS: 14

<210> SEQ ID NO 1
<211> LENGTH: 10
<212> TYPE: PRT
<213> ORGANISM: Unknown
<220> FEATURE:
<223> OTHER INFORMATION: GnRh-2

<400> SEQUENCE: 1

Glu His Trp Ser His Gly Trp Tyr Pro Gly
 1               5                  10

<210> SEQ ID NO 2
<211> LENGTH: 10
<212> TYPE: PRT
<213> ORGANISM: Unknown
<220> FEATURE:
<223> OTHER INFORMATION: GnRh-2 agonist
<220> FEATURE:
<221> NAME/KEY: VARIANT
<222> LOCATION: 5
<223> OTHER INFORMATION: Xaa = Tyr, His or Leu
<220> FEATURE:
<221> NAME/KEY: VARIANT
<222> LOCATION: 6
<223> OTHER INFORMATION: Xaa = D-Ala or D-Lys
<220> FEATURE:
<221> NAME/KEY: VARIANT
<222> LOCATION: 7
<223> OTHER INFORMATION: Xaa = Leu, Tyr or Trp
<220> FEATURE:
<221> NAME/KEY: VARIANT
<222> LOCATION: 8
<223> OTHER INFORMATION: Xaa = Leu, Tyr or Trp

<400> SEQUENCE: 2

Glu His Trp Ser Xaa Xaa Xaa Xaa Pro Gly
 1               5                  10

<210> SEQ ID NO 3
<211> LENGTH: 10
<212> TYPE: PRT
<213> ORGANISM: Unknown
<220> FEATURE:
<223> OTHER INFORMATION: GnRh-2 agonist
<220> FEATURE:
<221> NAME/KEY: VARIANT
<222> LOCATION: 6
<223> OTHER INFORMATION: Xaa = D-Ala

<400> SEQUENCE: 3

Glu His Trp Ser His Xaa Trp Tyr Pro Gly
 1               5                  10

<210> SEQ ID NO 4
<211> LENGTH: 10
<212> TYPE: PRT
<213> ORGANISM: Unknown
<220> FEATURE:
<223> OTHER INFORMATION: GnRh-2 agonist
<220> FEATURE:
```

```
<221> NAME/KEY: VARIANT
<222> LOCATION: 6
<223> OTHER INFORMATION: Xaa = D-Lys

<400> SEQUENCE: 4

Glu His Trp Ser His Xaa Trp Tyr Pro Gly
 1               5                  10

<210> SEQ ID NO 5
<211> LENGTH: 10
<212> TYPE: PRT
<213> ORGANISM: Unknown
<220> FEATURE:
<223> OTHER INFORMATION: GnRh-2 agonist
<220> FEATURE:
<221> NAME/KEY: VARIANT
<222> LOCATION: 6
<223> OTHER INFORMATION: Xaa = D-Ala

<400> SEQUENCE: 5

Glu His Trp Ser His Xaa Leu Tyr Pro Gly
 1               5                  10

<210> SEQ ID NO 6
<211> LENGTH: 10
<212> TYPE: PRT
<213> ORGANISM: Unknown
<220> FEATURE:
<223> OTHER INFORMATION: GnRh-2 agonist
<220> FEATURE:
<221> NAME/KEY: VARIANT
<222> LOCATION: 6
<223> OTHER INFORMATION: Xaa = D-Ala

<400> SEQUENCE: 6

Glu His Trp Ser Leu Xaa Trp Tyr Pro Gly
 1               5                  10

<210> SEQ ID NO 7
<211> LENGTH: 10
<212> TYPE: PRT
<213> ORGANISM: Unknown
<220> FEATURE:
<223> OTHER INFORMATION: GnRh-2 agonist
<220> FEATURE:
<221> NAME/KEY: VARIANT
<222> LOCATION: 6
<223> OTHER INFORMATION: Xaa = D-Ala

<400> SEQUENCE: 7

Glu His Trp Ser Tyr Xaa Trp Leu Pro Gly
 1               5                  10

<210> SEQ ID NO 8
<211> LENGTH: 10
<212> TYPE: PRT
<213> ORGANISM: Unknown
<220> FEATURE:
<223> OTHER INFORMATION: GnRh-2 agonist
<220> FEATURE:
<221> NAME/KEY: VARIANT
<222> LOCATION:
<223> OTHER INFORMATION: Xaa = D-Ala

<400> SEQUENCE: 8

Glu His Trp Ser His Xaa Tyr Trp Pro Gly
 1               5                  10

<210> SEQ ID NO 9
```

```
<211> LENGTH: 10
<212> TYPE: PRT
<213> ORGANISM: Unknown
<220> FEATURE:
<223> OTHER INFORMATION: GnRh-2 antagonist
<220> FEATURE:
<221> NAME/KEY: VARIANT
<222> LOCATION: 1
<223> OTHER INFORMATION: Xaa = D-alanine substituted with naphthyl on
      the beta-carbon atom further substituted with an acetyl group
<220> FEATURE:
<221> NAME/KEY: VARIANT
<222> LOCATION: 2
<223> OTHER INFORMATION: Xaa = D-alanine substituted with pyridyl on the
      beta-carbon atom linked to the 3-position on the pyridine ring
<220> FEATURE:
<221> NAME/KEY: VARIANT
<222> LOCATION: 3
<223> OTHER INFORMATION: Xaa = D-3Pal
<220> FEATURE:
<221> NAME/KEY: VARIANT
<222> LOCATION: 5
<223> OTHER INFORMATION: Xaa = Tyr or His
<220> FEATURE:
<221> NAME/KEY: VARIANT
<222> LOCATION: 6
<223> OTHER INFORMATION: Xaa = D-isomer of citrulline
<220> FEATURE:
<221> NAME/KEY: VARIANT
<222> LOCATION: 8
<223> OTHER INFORMATION: Xaa = Tyr or Leu
<220> FEATURE:
<221> NAME/KEY: VARIANT
<222> LOCATION: 10
<223> OTHER INFORMATION: Xaa = D-Ala

<400> SEQUENCE: 9

Xaa Xaa Xaa Ser Xaa Xaa Trp Xaa Pro Xaa
 1               5                   10

<210> SEQ ID NO 10
<211> LENGTH: 10
<212> TYPE: PRT
<213> ORGANISM: Unknown
<220> FEATURE:
<223> OTHER INFORMATION: GnRh-2 antagonist
<220> FEATURE:
<221> NAME/KEY: VARIANT
<222> LOCATION: 1
<223> OTHER INFORMATION: Xaa = D-alanine substituted with naphthyl on
      the beta-carbon atom further substituted with an acetyl group
<220> FEATURE:
<221> NAME/KEY: VARIANT
<222> LOCATION: 2
<223> OTHER INFORMATION: Xaa = D-alanine substituted with pyridyl on the
      beta-carbon atom linked to the 3-position on the pyridine ring
<220> FEATURE:
<221> NAME/KEY: VARIANT
<222> LOCATION: 3
<223> OTHER INFORMATION: Xaa = D-3Pal
<220> FEATURE:
<221> NAME/KEY: VARIANT
<222> LOCATION: 6
<223> OTHER INFORMATION: Xaa = D-isomer of citrulline
<220> FEATURE:
<221> NAME/KEY: VARIANT
<222> LOCATION: 10
<223> OTHER INFORMATION: Xaa = D-Ala

<400> SEQUENCE: 10

Xaa Xaa Xaa Ser Tyr Xaa Trp Tyr Pro Xaa
 1               5                   10

<210> SEQ ID NO 11
<211> LENGTH: 10
```

```
<212> TYPE: PRT
<213> ORGANISM: Unknown
<220> FEATURE:
<223> OTHER INFORMATION: GnRh-2 antagonist
<220> FEATURE:
<221> NAME/KEY: VARIANT
<222> LOCATION: 1
<223> OTHER INFORMATION: Xaa = D-alanine substituted with naphthyl on
      the beta-carbon atom further substituted with an acetyl group
<220> FEATURE:
<221> NAME/KEY: VARIANT
<222> LOCATION: 2
<223> OTHER INFORMATION: Xaa = D-alanine substituted with pyridyl on the
      beta-carbon atom linked to the 3-position on the pyridine ring
<220> FEATURE:
<221> NAME/KEY: VARIANT
<222> LOCATION: 3
<223> OTHER INFORMATION: Xaa = D-3Pal
<220> FEATURE:
<221> NAME/KEY: VARIANT
<222> LOCATION: 6
<223> OTHER INFORMATION: Xaa = D-isomer of citrulline
<220> FEATURE:
<221> NAME/KEY: VARIANT
<222> LOCATION: 10
<223> OTHER INFORMATION: Xaa = D-Ala

<400> SEQUENCE: 11

Xaa Xaa Xaa Ser His Xaa Trp Tyr Pro Xaa
1               5                   10

<210> SEQ ID NO 12
<211> LENGTH: 10
<212> TYPE: PRT
<213> ORGANISM: Unknown
<220> FEATURE:
<223> OTHER INFORMATION: GnRh-2 antagonist
<220> FEATURE:
<221> NAME/KEY: VARIANT
<222> LOCATION: 1
<223> OTHER INFORMATION: Xaa = D-alanine substituted with naphthyl on
      the beta-carbon atom further substituted with an acetyl group
<220> FEATURE:
<221> NAME/KEY: VARIANT
<222> LOCATION: 2
<223> OTHER INFORMATION: Xaa = D-alanine substituted with pyridyl on
      the beta-carbon atom linked to the 3-position on the pyridine ring
<220> FEATURE:
<221> NAME/KEY: VARIANT
<222> LOCATION: 3
<223> OTHER INFORMATION: Xaa = D-3Pal
<220> FEATURE:
<221> NAME/KEY: VARIANT
<222> LOCATION: 6
<223> OTHER INFORMATION: Xaa = D-isomer of citrulline
<220> FEATURE:
<221> NAME/KEY: VARIANT
<222> LOCATION: 10
<223> OTHER INFORMATION: Xaa = D-Ala

<400> SEQUENCE: 12

Xaa Xaa Xaa Ser Tyr Xaa Trp Leu Pro Xaa
1               5                   10

<210> SEQ ID NO 13
<211> LENGTH: 10
<212> TYPE: PRT
<213> ORGANISM: Unknown
<220> FEATURE:
<223> OTHER INFORMATION: GnRH-1

<400> SEQUENCE: 13

Glu His Trp Ser Tyr Gly Leu Arg Pro Gly
1               5                   10
```

```
<210> SEQ ID NO 14
<211> LENGTH: 10
<212> TYPE: PRT
<213> ORGANISM: Unknown
<220> FEATURE:
<223> OTHER INFORMATION: GnRh-3

<400> SEQUENCE: 14

Glu His Trp Ser Tyr Gly Trp Leu Pro Gly
 1               5                  10
```

AGONISTS AND ANTAGONISTS OF GONADOTROPIN-RELEASING HORMONE-2, AND USE THEREOF

BACKGROUND OF THE INVENTION (a) Field of the Invention

The present invention relates to agonists and antagonists of gonadotropin-releasing hormone-2 (GnRH-2) which regulate the activity of GnRH-2 by specifically binding to GnRH-2 receptors, and pharmaceutical compositions for regulating the GnRH-2 receptors.

(b) Description of the Related Art

Gonadotropin-releasing hormone (GnRH) is a neuropeptide having an important role in reproductive physiology, and it is widely used as a treatment agent for endocrinal and neuroendocrinal diseases (Sealfon S C, et al., Endocr. Rev. vol.18 pp. 180-205, 1997). Thus far, about 14 forms of GnRH have been found in 70 different species of vertebrates and invertebrates, and two or more GnRHs exist in each individual (Fernald R D, et al., Front Neuroendocrinol, vol.20, pp. 224-240, 1999).

The first type of GnRH (GnRH-1) is a hypothalamic GnRH. The neurons of GnRH-1 are mostly distributed in the hypothalamus, and their nerve terminals exist at the median eminence. GnRH-1 is secreted at the median eminence, arrives at the pituitary gland via a portal system that connects the hypothalamus and pituitary gland, and regulates the functions of the pituitary gland. GnRH-1 regulates the secretion of follicle stimulating hormone (FSH) and luteinizing hormone (LH), and LH and FSH regulate gonadal development and steroid synthesis. Therefore, GnRH-1 is deeply involved in the regulation of reproductive endocrinology in vertebrates (Seeburg P H, et al., Recent Prog Horm Res vol.43 pp. 69-98, 1986).

The typical GnRH-1 is mammalian GnRH (mGnRH) that was found for the first time in the mammalian hypothalamus (Matsuo H, et al., Biochem Biophys Res Commun vol.43 pp. 1334-1339, 1971; Burgus R, et al., Proc Natl Acad Sci USA vol.69 pp. 278-282, 1972). mGnRH is found in most vertebrates including Aves, Reptilia, and Amphibia, as well as Mammalia. However, in fish several birds, and amphibians, different forms thereof are found (Miyamoto K, et al., Life Sci vol. 32, pp. 1341-1347, 1983; Powell J F et al., Proc Natl Acad Sci USA vol. 91 pp. 12081-12085, 1994; Yoo M S, et al., Mol Cell Endocrinol vol.164 pp. 197-204, 2000).

The second type of. GnRH (GnRH-2) is chicken GnRH-II ($His^5Trp^7Tyr^8$GnRH, cGnRH-II) that was found for the first time in the chick brain (Miyamoto K et al, Proc Natl Acad Sci USA vol.81 pp. 3874-3878). The neurons of cGnRH-II are mostly found in the midbrain, and their nerve terminals exist in the posterior hypothalamus or hindbrain. Although the exact functions of cGnRH-II are not well known, it is postulated that it generally has an important role in functioning as a neuromodulator and in regulating sexual behaviors (Troskie B, et al., Neuroendocrinology vol.65 pp. 396-402, 1997). Further, as several nerve terminals extend to the hypothalamus, it is probably involved the regulation of reproductive physiology. cGnRH-II is found in almost all vertebrates, i.e., Pisces, Amphibia, and Reptilia, as well as Mammalia including humans, and mutant forms thereof have not been found (White R B, et al., Proc Natl Acad Sci USA vol.95 pp. 305-309, 1998).

Hence, in vertebrates higher than Pisces, GnRHs that exist in a single species are cGnRH-II (GnRH-2) and mGnRH (or a mutant form of GnRH-1). Furthermore, GnRH-1 and GnRH-2 have been known to be expressed in peripheral tissues of the body, in addition to the central nervous system. Particularly, the expression of GnRH-1 and GnRH-2 has been reported in tissues regulating the immune and reproductive systems (Kang S K, et al., Endocrinology vol.142 pp. 182-192, 2001; Wilson T M, et al., Mol Endocrinol vol.9 pp. 44-53, 1995; Dong K W, et al., Mol Cell Endocrinol vol.117 pp. 121-130, 1996). Therefore, GnRH is expected to function as a local regulator in immune and reproductive systems, in addition to its functions in the neuroendocrine regulation.

Studies of GnRH have been vigorously conducted, as they provide essential information on the design of clinical treatment agents as well as the understanding of reproductive functions. GnRH is secreted in a pulsatile manner, and such a secretion manner plays an important role in regulating the synthesis and secretion of steroid hormones in the gonads and maintaining normal reproductive functions. Endocrine or neuroendocrine diseases generated by the modification of GnRH genes and dysfunction of GnRH neurons can be cured by treating GnRH in a pulsatile manner. However, if GnRH is treated continuously at a high concentration, the function of GnRH receptors becomes deficient, and ultimately hypofunction of the gonads is induced. By virtue of such GnRH functions, GnRH is used for the treatment of reproductive endocrine diseases and precocious puberty, as well as the control of menstruation periods in in vitro fertilization (Huirne J A, et al., Lancet vol.358 pp. 1793-1803, 2001). Also, GnRH is used for the treatment of cancers that are sensitive to steroid hormones, i.e., prostate cancer, breast cancer, and ovarian cancer (Schally A V, Peptides vol.20 pp. 1247-1262, 1999; Grundker C, et al., Eur J Endocrinol vol.146 pp. 1-14, 2002).

Recent studies have revealed that GnRH-2 is more effective than GnRH-1 for the treatment of some cancer cells, and that signal transduction via GnRH-2 is different from that of GnRH-1 (Kang et al., ibid.; Grundker et al., ibid.). Also, as a receptor sensitive to GnRH-2 was identified in monkeys (Neill J D, et al., Biochem Biophys Res Commun vol. 282 pp. 1012-1018, 2001; Millar R, et al., Proc Natl Acad Sci USA vol. 98 pp. 9636-9641, 2001), studies about the physiological functions of GnRH-2 via such receptor became necessary. Due to the clinical importance of GnRH, approximately 3000 GnRH agonists and antagonists have been developed thus far. Most GnRH agonists and antagonists were developed by partially modifying the amino acid structure of GnRH-1 to increase their binding affinity toward the GnRH receptors and to slow down their in vivo degradation rate, thereby maximizing their efficiency (Sealfon et al., ibid.).

Recently, the inventors cloned three types of receptors that are very sensitive to GnRH-2 in bullfrogs (Wang et al., Proc Natl Acad Sci USA vol. 98 pp. 361-366, 2001). All of the bullfrog GnRH receptors (bfGnRHR) react more sensitively to GnRH-2 than GnRH-1. Also, the bfGnRHR shows great structural differences from the GnRH receptors that were found in mammals, but it is very similar in structural aspects to the GnRH receptors found in nonmammals, i.e., Pisces, Amphibia, and Aves. In addition, it is structurally similar to the receptor sensitive to GnRH-2 that has been recently found in monkeys (monkey GnRHR-2) (Neill et al., ibid.; Millar et al., ibid.). Accordingly, the bfGnRHR is very similar to the second GnRH receptor of mammals in respect of its structure and function.

Thousands of GnRH-1 agonists have been developed because of the reproductive and physiological importance of GnRH-1, as well as its clinical efficacy in reproductive dysfunction and cancer treatment. However, little development and study of GnRH-2 analogs has been conducted, for several reasons. GnRH-2 was characterized relatively later than GnRH-1, and the fact that GnRH-2 is present in most vertebrates including humans was revealed only four years ago. In addition, in vivo functions of GnRH-2 have not been fully known, and the discovery of the GnRH-2 receptor which is the most important factor in the development of GnRH-2 analogs was delayed. In nonmammalian animals, the GnRH-2 receptors were found in catfish in 1997 and goldfish in 1998 (Tensen et al., 1997; Illing et al., 1999), and recently three types of GnRH receptors were found in bullfrogs by the inventors, and thereby studies on them became serious (Wang et al., ibid.). Moreover, in the case of mammals, the fact that the second receptor that is sensitive to GnRH-2 is present in monkeys was found extremely recently (Millar et al., ibid.; Neill et al., ibid.]. Hence, studies regarding the development of GnRH-2 analogs have been delayed.

Several GnRH-2 agonists were developed through the substitution of the $6^{th}$ amino acid of GnRH-2 ([D-Arg$^6$]GnRH-2, [D-Leu$^6$]GnRH-2, [D-Trp$^6$]GnRH-2, [D-t-bu-Ser$^6$]GnRH-2, Siler-Khodr and Khodr, et al., ibid. and PCT Laid-Open Publication WO No. 01-74377). However, these agonists studies were carried out in cell lines having receptors sensitive to GnRH-1, and they were not conducted with regard to receptors sensitive to GnRH-2.

Therefore, the current circumstance is that the development of GnRH-1 antagonists and studies about GnRH-2 receptors have been carried out, but the development of GnRH-2 agonists and antagonists has not been conducted. Hence, for clinical applications and studies of physiological functions via GnRH-2, the development of GnRH-2 agonists and antagonists is required.

SUMMARY OF THE INVENTION

In order to achieve the objects as mentioned above, it is an object of the present invention to provide agonists of gonadotropin-releasing hormone-2 (GnRH-2) which regulate the activity of GnRH-2 by specifically binding to GnRH-2 receptors.

It is another object of the invention to provide antagonists of gonadotropin-releasing hormone-2 (GnRH-2) which inhibit the activity of GnRH-2 by specifically binding to GnRH-2 receptors.

It is a further object of the invention to provide pharmaceutical compositions for regulating the release of gonadotropin comprising the GnRH-2 antagonists or agonists as active ingredients.

In order to achieve the objects as mentioned above, the present invention relates to agonists of gonadotropin-releasing hormone-2 (GnRH-2) which regulate the activity of GnRH-2 by specifically binding to GnRH-2 receptors.

Also, the invention relates to a pharmaceutical composition for regulating the release of gonadotropin comprising the GnRH-2 agonists as an active ingredient, and pharmaceutically acceptable carriers.

Also, the invention relates to antagonists of gonadotropin-releasing hormone-2 (GnRH-2) which regulate the activity of GnRH-2 by specifically binding to GnRH-2 receptors.

Also, the invention relates to a pharmaceutical composition for regulating the release of gonadotropin comprising the GnRH-2 antagonists as an active ingredient, and pharmaceutically acceptable carriers.

BRIEF DESCRIPTION OF THE DRAWINGS

FIG. 1 shows the sequences of GnRH-1, GnRH-2, and their analogs (SEQ ID NOs: 1-13 and 15).

DETAILED DESCRIPTION OF THE PREFERRED EMBODIMENTS

Figure 2A:
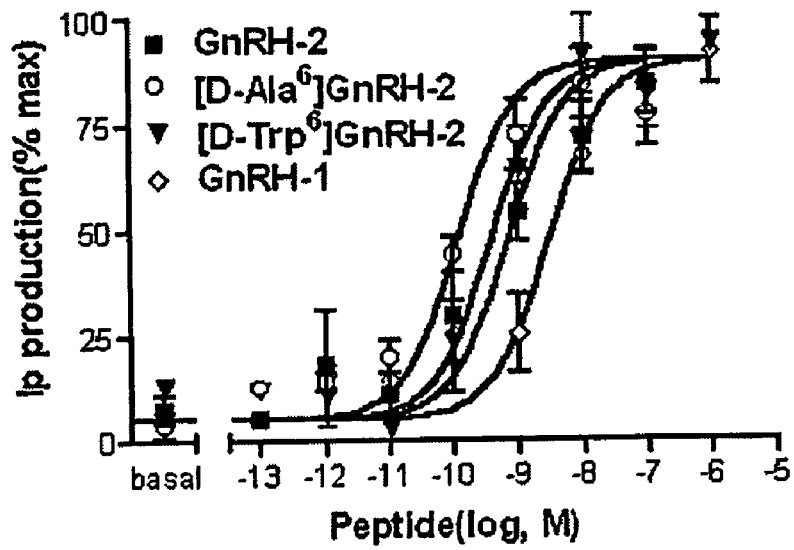
FIG. 2a to FIG. 2d are graphs showing the inositol phosphate production after treating GnRH-1, GnRH-2, and GnRH-2 agonists to each cell line expressing the GnRH-2 receptors, i.e., bfGnRHR-1, bfGnRHR-2, and bfGnRHR-3, and the GnRH receptor of rats.
Figure 2B:
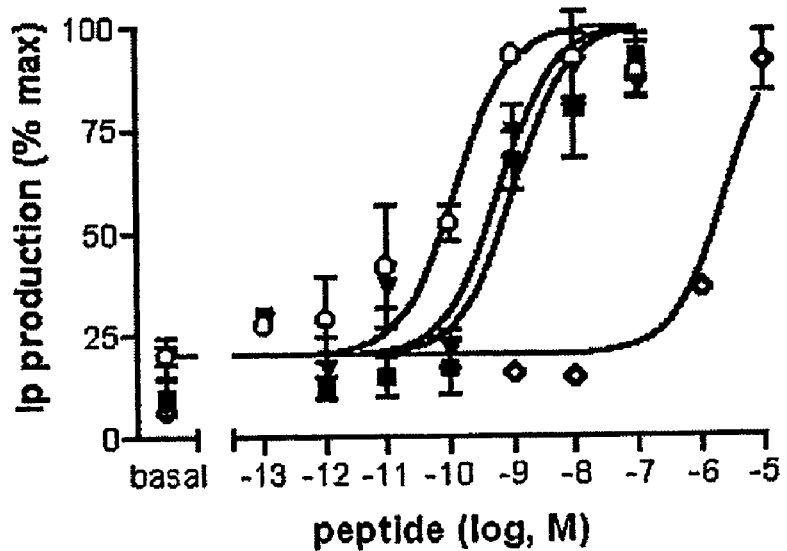

The inventors recently identified three types of GnRH receptors (bfGnRHR) that are very sensitive to GnRH-2 in bullfrogs for the first time (Wang et al., ibid), and they recently cloned a receptor that is sensitive to GnRH-2 in the genome of cells in Primates. The amino acid sequence of this receptor differs by two amino acids from that of the Primate GnRH-2 receptor that has already been characterized (Neill et al., ibid.). By using them, the inventors constructed cell lines expressing rat GnRH receptors, which very sensitively react to GnRH-1, and bfGnRHR, which sensitively reacts to GnRH-2, by the retrovirus-mediated infection method, and investigated the activities of the receptors by treating them with GnRH-2 agonists or antagonists. Also, cells expressing the GnRH-2 receptor that was found in Primates were treated with GnRH-2 and its agonists to determine the luciferase activities. As a result, it was revealed that the inositol phosphate production and the luciferase activity were increased depending on the concentration of these agonists and antagonists. [D-Ala$^6$]GnRH-2 had higher specific sensitivity than a wild type ligand; and the inventors found that Trptorelix-1 and Trptorelix-2, which are antagonists of GnRH-2, show very high sensitivity as compared with Cetrorelix, which was already known for a GnRH-1 antagonist, and that they inhibit the activity of GnRH-2 receptors, and thus completed the present invention.

Hereafter, the present invention will be described in more detail.

The present invention provides agonists of GnRH-2 that regulate the activity of GnRH-2 by specifically binding to GnRH-2 receptors. The amino acid sequences of GnRH-1 and GnRH-2 in mammals including humans are shown below and in FIG. 1. The amino acid sequences of GnRH-1 and GnRH-2 show differences at the $5^{th}$, $7^{th}$, and $8^{th}$ amino acids.

GnRH-1: pGlu-His-Trp-Ser-Tyr-Gly-Leu-Arg-Pro-GlyNH$_2$ (SEQ ID NO: 13).

GnRH-2 (SEQ ID NO: 1): pGlu-His-Trp-Ser-His-Gly-Trp-Tyr-Pro-GlyNH$_2$

Preferably, the GnRH-2 agonists according to the present invention are peptides where the $6^{th}$ amino acid of the GnRH-2 is D-Ala or D-Lys, and more preferably they have a peptide sequence (SEQ ID NO: 2) as shown below. [D-Lys$^6$]GnRH-2 shown in SEQ ID NO: 4 is a peptide In which D-Ala is modified into D-Lys at the $6^{th}$ amino acid, and all other sequences shown in SEQ ID NO: 3 and SEQ ID NOS: 5 to 8 are those whose $6^{th}$ amino acid is substituted with D-Ala.

pyroGlu-His-Trp-Ser-Xaa$_5$-Xaa$_6$-Xaa$_7$-Xaa$_8$-Pro-GlyNH$_2$

In the above peptide sequence,

Xaa$_5$ is Tyr, His, or Leu;

Xaa$_6$ is D-Ala, or D-Lys;

Xaa$_7$ is Leu, Tyr, or Trp; and

Xaa$_8$ is Leu, Tyr, or Trp.

Most preferably, the GnRH-2 agonists are selected from the group consisting of the peptides shown in SEQ ID NO: 3 to SEQ ID NO: 8, and these sequences are illustrated below. In the amino acid sequences of GnRH-2 agonists shown below, amino acids that are different from the amino acid sequence of GnRH-2 are represented in bold Italics.

[D-Ala$^6$]GnRH-2(SEQ NO: 3): p-Glu-His-Trp-Ser-His-*D-Ala*-Trp-Tyr-Pro-GlyNH$_2$

[D-Lys$^6$]GnRH-2(SEQ ID NO: 4): p-Glu-His-Trp-Ser-His-*D-Lys*-Trp-Tyr-Pro-Gly-NH$_2$

[D-Ala$^6$, Leu$^7$]GnRH-2(SEQ ID NO: 5): pGlu-His-Trp-Ser-His-*D-Ala-Leu*-Tyr-Pro-Gly-NH$_2$

[Leu$^5$, D-Ala$^6$]GnRH-2(SEQ ID NO: 6): pGlu-His-Trp-Ser-*Leu-D-Ala*-Trp-Tyr-Pro-Gly-NH$_2$

[Tyr$^5$, D-Ala$^6$, Leu$^6$]GnRH-2(SEQ ID NO: 7): pGlu-His-Trp-Ser-*Tyr-D-Ala*-Trp-*Leu*-Pro-Gly-NH$_2$

[D-Ala6, Tyr$^7$, Trp$^8$]GnRH-2(SEQ ID NO: 8): pGlu-His-Trp-Ser-His-*D-Ala-Tyr-Trp*-Pro-Gly-NH$_2$.

[Tyr$^5$, D-Ala$^6$, Leu$^8$]GnRH-2 is a peptide in which the $6^{th}$ amino acid in salmon GnRH, which is GnRH-3, is modified into D-Ala; Trp at the $7^{th}$ position is that of GnRH-2; the $5^{th}$ amino acid is Tyr that is found in GnRH-1; and the $8^{th}$ amino acid is Leu of GnRH-3. [D-Ala$^6$, Tyr$^7$, Trp$^8$]GnRH-2 is an analog in which the $7^{th}$ and $8^{th}$ amino acids of GnRH-2 are substituted with each other, while [Leu$^5$, D-Ala$^6$]GnRH-2 is a GnRH-2 analog whose $5^{th}$ amino acid is substituted with Leu.

Gly, the $6^{th}$ amino acid of GnRH-2, is a position on which a beta-II-turn is formed when the GnRH binds to its receptor. The substitution of Gly with D-Ala contributes to a stable beta-II-turn conformation of GnRH. In the case of [D-Trp$^6$]GnRH-2 where said Gly is substituted with D-Trp, it shows a binding affinity and sensitivity similar to those of GnRH-2, whereas [D-Ala$^6$]GnRH-2 shows a much higher binding affinity and sensitivity than GnRH-2. Consequently, D-Ala substitution is regarded to increase the interaction with the receptors.

Also, the present invention relates to GnRH-2 (gonadotropin-releasing hormone-2) antagonists which inhibit the activity of GnRH-2 by specifically binding to GnRH receptors, and the GnRH-2 antagonists are preferably GnRH-2 antagonists comprising the following peptide sequence (SEQ ID NO: 9).

Ac-D-2Nal-(A)-D-Phe-D-3Pal-Ser-Xaa$_5$-D-Cit-Trp-Xaa$_8$-Pro-D-AlaNH$_2$

In the above peptide sequence,

A is 4Cl, 4F, or 4Br, and preferably 4Cl;

Xaa$_5$ is Tyr or His; and

Xaa$_8$ is Tyr or Leu.

The above-modified amino acids are compound names that are widely used in the art to which the invention pertains, and specifically, Ac-D-Nal refers to D-alanine which is substituted with a naphthyl on the beta-carbon atom and is further substituted with an acetyl group (β-(2-naphthyl-D-Ala)); D-3Pal refers to D-alanine which is substituted with a pyridyl on the beta-carbon atom linked to the 3-position on the pyridine ring; and D-cit refers to a D-isomer of citrulline.

Most preferably, the GnRH-2 antagonists are selected from the group consisting of peptides shown in SEQ ID NO: 10 to SEQ ID NO: 12. The GnRH-2 antagonists shown in SEQ ID NOS: 10 to 12 are named Trptorelix. These amino acid sequences are illustrated below, and in the amino acid sequences of Trptorelix-2 and Trptorelix-3, amino acids different from the amino acid sequence of Trptorelix-1 are represented in bold Italics.

Trptorelix-1 (SEQ ID NO: 10): Ac-D2Nal-(4Cl)D-Phe-D-3Pal-Ser-Tyr-D-Cit-Trp-Tyr-Pro-DAlaNH$_2$ Trptorelix-2(SEQ ID NO: 11): Ac-D2Nal-(4Cl)D-Phe-D-3Pal-Ser-*His*-DCit-Trp-Tyr-Pro-DAla-NH$_2$ Trptorelix-3(SEQ ID NO: 12): Ac-D2Nal-(4Cl)D-Phe-D-3Pal-Ser-Tyr-DCit-Trp-*Leu*-Pro-DAla-NH$_2$.

The GnRH-2 antagonists called Trptorelix are characterized by having Trp as their $7^{th}$ amino acid, and this is common to GnRH-2 and salmon GnRH (found only in fish, pyroGlu-His-Trp-Ser-Tyr-Gly-Trp-Leu-Pro-GlyNH$_2$ (SEQ ID NO: 14).

Trptorelix was constructed by modifying Cetrorelix (FIG. 1), a well-known antagonist of GnRH-1. Cetrorelix is an antagonist constructed by substituting the $1^{st}$, $2^{nd}$, $3^{rd}$, and $6^{th}$ amino acids GnRH-1 with amino acid derivatives, and it shows a high binding affinity toward GnRH-1 receptors but does not activate the receptors. Trptorelix-1 was synthesized by substituting the $7^{th}$ and $8^{th}$ amino acids of Cetrorelix, which are very important in binding to the GnRH-1 receptors, and thus this portion was changed to the amino acids of GnRH-2 to increase the binding affinity toward the GnRH-2 receptors (FIG. 1).

Figure 2C:
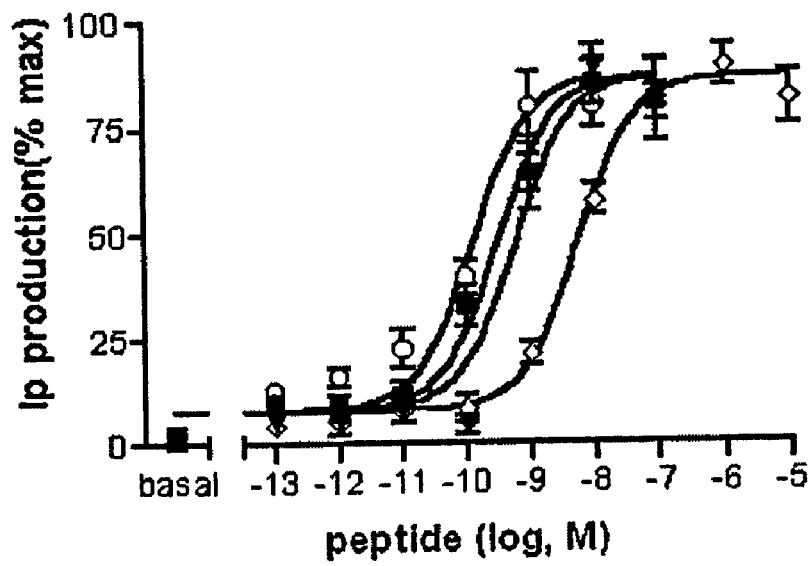
Figure 2D:
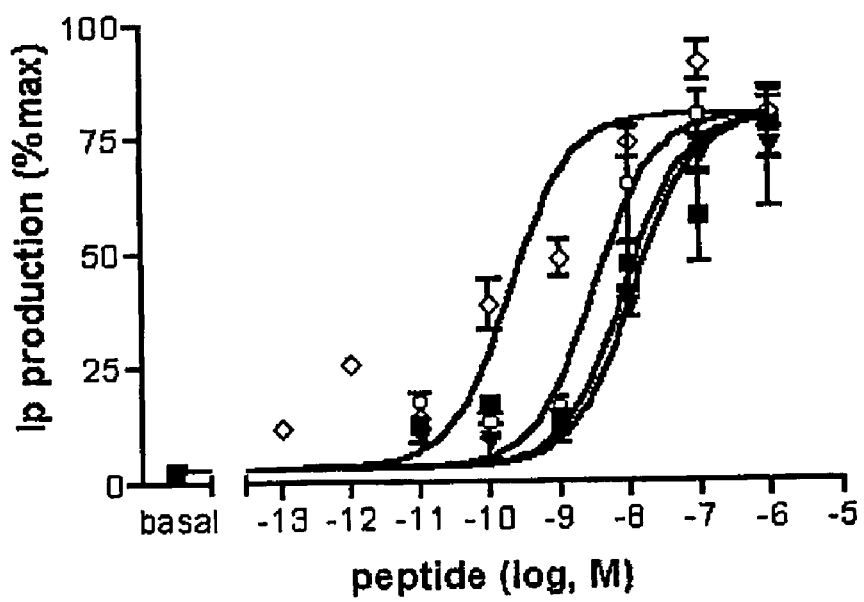

Cell lines expressing the rat GnRH receptor, which very sensitively reacts to GnRH-1, and bfGnRHR, which readily reacts to GnRH-2, were constructed by the retrovirus-mediated infection method, and they were treated with [D-Ala$^6$]GnRH-2 and [D-Trp$^6$]GnRH-2, which are GnRH-2 agonists, and Trptorelix-1, which is a GnRH-2 antagonist, to investigate the activity of the receptors. As a result, [D-Ala$^6$]GnRH-2 increased the amount of inositol phosphate in a concentration-dependent manner in the cells expressing bfGnRHR and showed a 2.5~10-fold higher sensitivity than GnRH-2, and a 40~20,000-fold higher sensitivity than GnRH-1 (FIG. 2a and FIG. 2c). On the other hand, in the cells expressing the rat GnRH receptor, [D-Ala$^6$]GnRH-2 showed a 5-fold higher sensitivity than GnRH-2 whereas it showed a 3.5-fold lower sensitivity than GnRH-1 (FIG. 2d). These results show that [D-Ala$^6$]GnRH-2 is a strong agonist specific to GnRH-2.

Figure 3A:
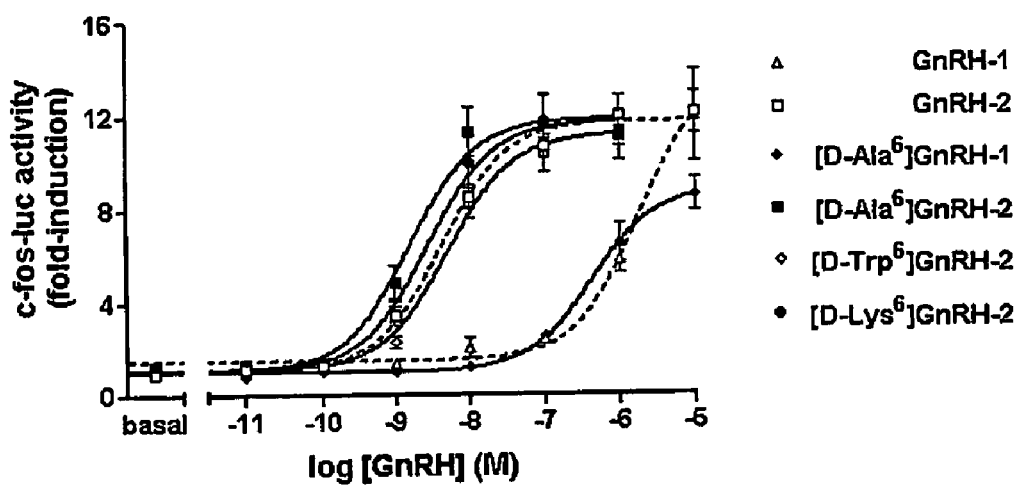
FIG. 3a to FIG. 3b show luciferase activity after treating GnRH-2 and GnRH-2 agonists to cells expressing the GnRH-2 receptor that was found in Primates.
Figure 3B:
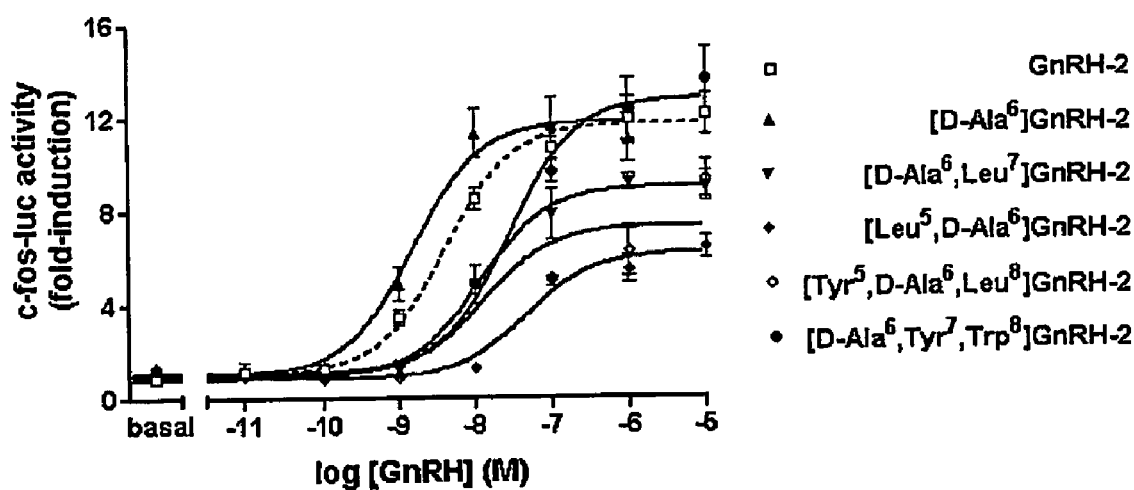

Also, in the cells expressing the Primate GnRH-2 receptor, [D-Ala$^6$]GnRH-2 showed about a 3-fold excellent effect as compared with GnRH-2. On the other hand, it was revealed that [D-Lys$^6$]GnRH-2 had about a 1.5-fold lower effect than GnRH-2, and that [D-Trp$^6$]GnRH-2 had a 1.2-fold lower effect than GnRH-2. Accordingly, these results suggest that with regard to the GnRH-2 receptors that are found in Primates and non-mammals, [D-Ala$^6$]GnRH-2 is the most effective agonist. Further, when analogs where the 5$^{th}$, 7$^{th}$, and 8$^{th}$ amino acids of [D-Ala$^6$]GnRH-2 are substituted were used, their effects were observed to be weaker than [D-Ala$^6$]GnRH-2, and it can therefore be seen that it is important to maintain His, Trp, and Tyr that are found at the 5$^{th}$, 7$^{th}$, and 8$^{th}$ positions of GnRH-2 as they are (FIG. 3b).

Figure 4:
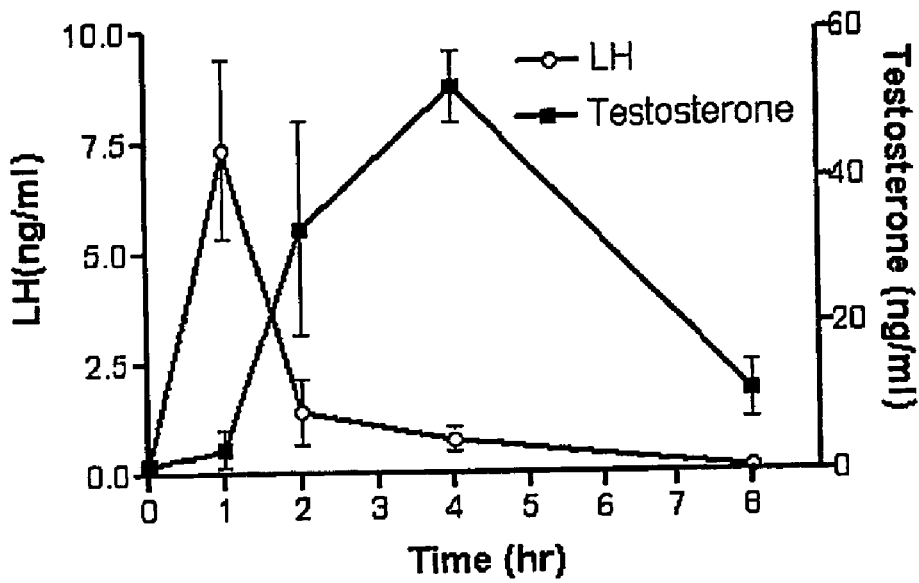
FIG. 4 shows the concentration of serum LH (luteinizing hormone) and testosterone over the lapse of time after treating 10 μg of a GnRH-2 agonist ([D-Ala$^6$]GnRH-2) into a rat.

[D-Ala$^6$]GnRH-2 showed in vivo effects. When 10 μg of [D-Ala$^6$]GnRH-2 were injected into a male rat, an increase in luteinizing hormone (LH) was observed in just one hour. This effect, however, was rapidly reduced after 2 hours from the injection. On the other hand, testosterone, which is a male hormone, began to rapidly increase from 2 hours after the injection, it arrived at a peak point in 4 hours, and it exhibited a significantly high value even after 8 hours as compared with before the injection (FIG. 4).

Figure 5A:
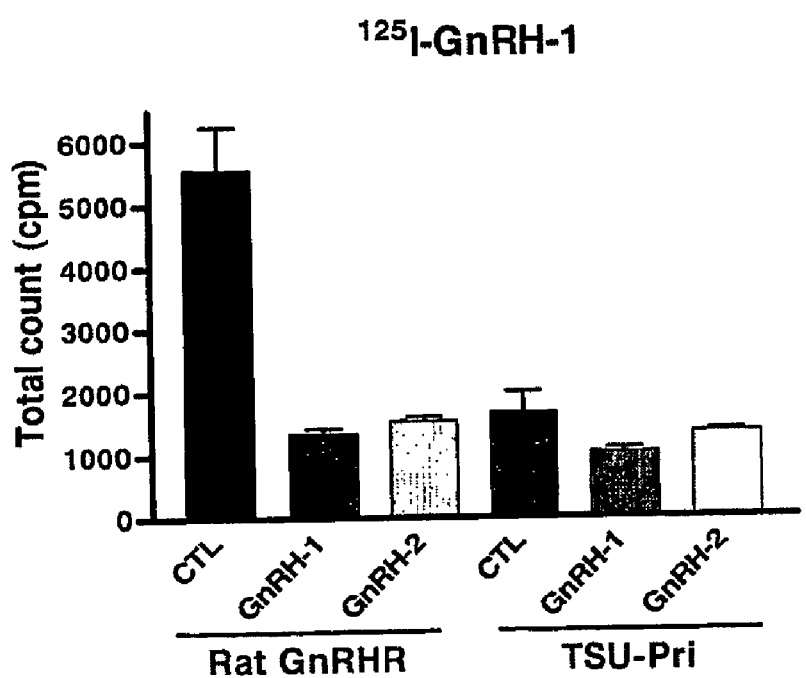
FIG. 5a to FIG. 5c show that a receptor selectively binding to GnRH-2 is present in TSU-Pri cells, human prostate cancer cells.
Figure 5B:
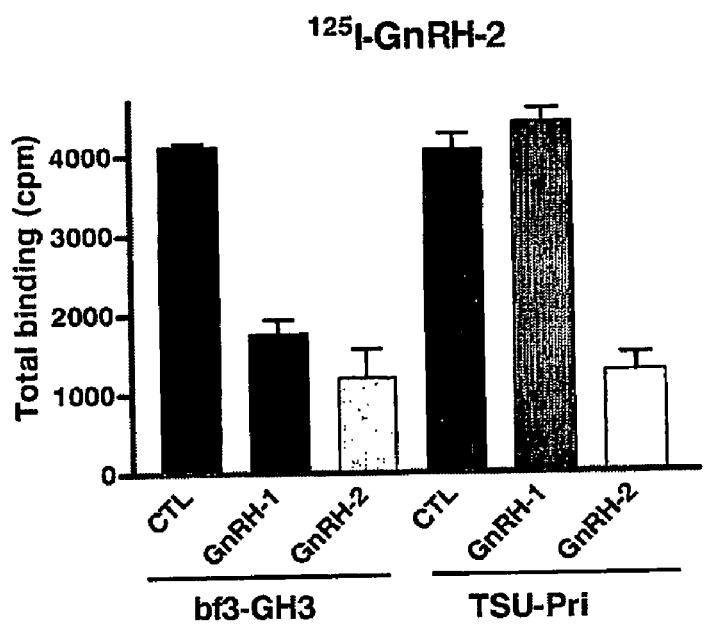
Figure 5C:
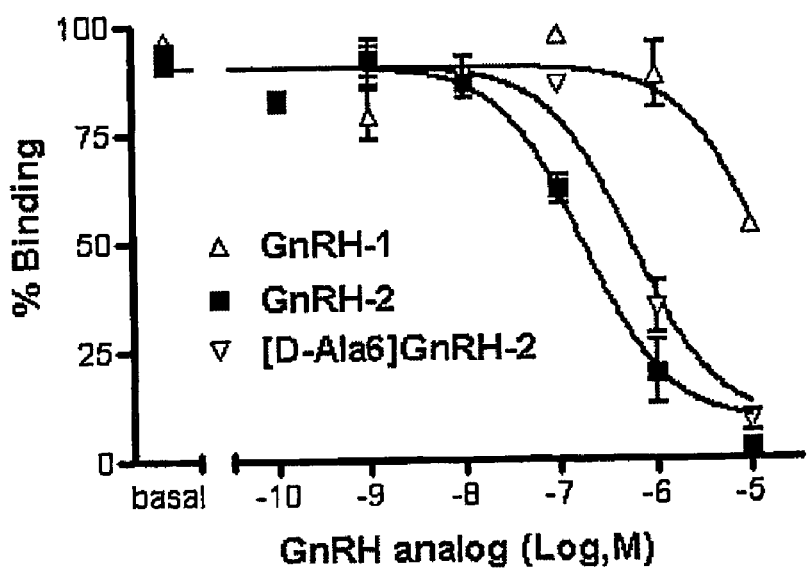

The inventors revealed that a receptor with regard to GnRH-2 is present in prostate cancer cells. When TSU-Pri cells, which are cultured prostate cancer cells, were treated with I$^{152}$-radiolabeled GnRH-1, no binding with cells was observed, but when they were treated with I$^{152}$-radiolabeled GnRH-2, binding with cells was observed (FIG. 5a and FIG. 5b). In the latter case, when unradiolabeled [D-Ala$^6$]GnRH-2 was treated, the binding of I$^{152}$-radiolabeled GnRH-2 was reduced in a concentration-dependent manner (FIG. 5c). These results show that a receptor for GnRH-2 is present in prostate cancer cells and suggest that [D-Ala$^6$]GnRH-2 can be used for the treatment of prostate cancer.

Figure 6A:
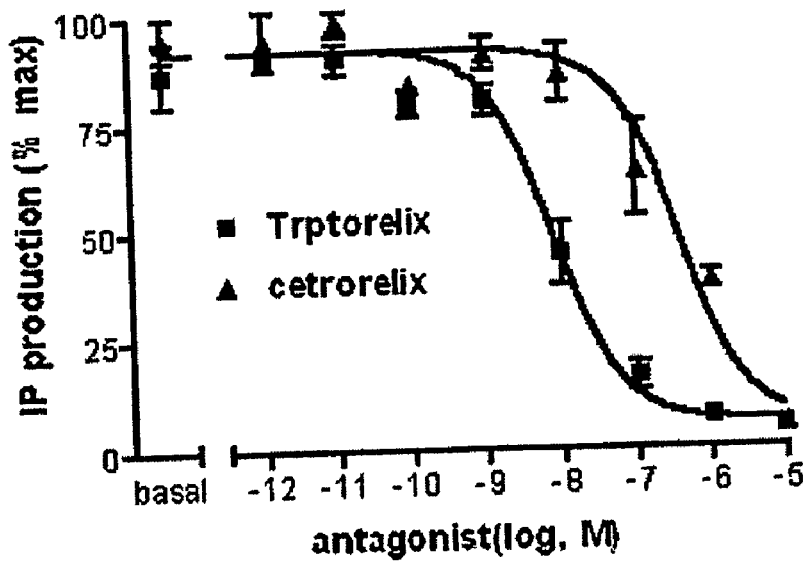
FIG. 6a to FIG. 6c are graphs showing the inositol phosphate production after treating Trptorelix-1 or Cetrorelix in the presence of 10 nM GnRH-2 to GH3 each cell line expressing the GnRH-2 receptors, i.e., bfGnRHR-2 and bfGnRHR-3, and rat GnRH receptor.
Figure 6B:
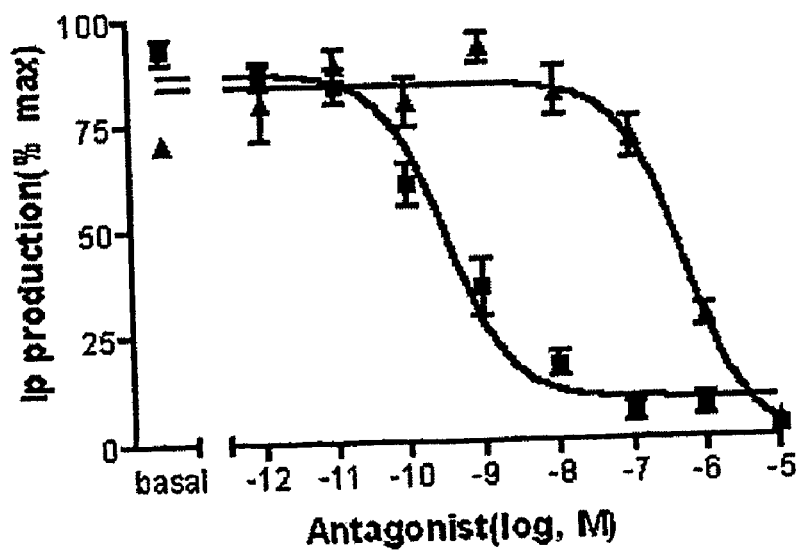
Figure 6C:
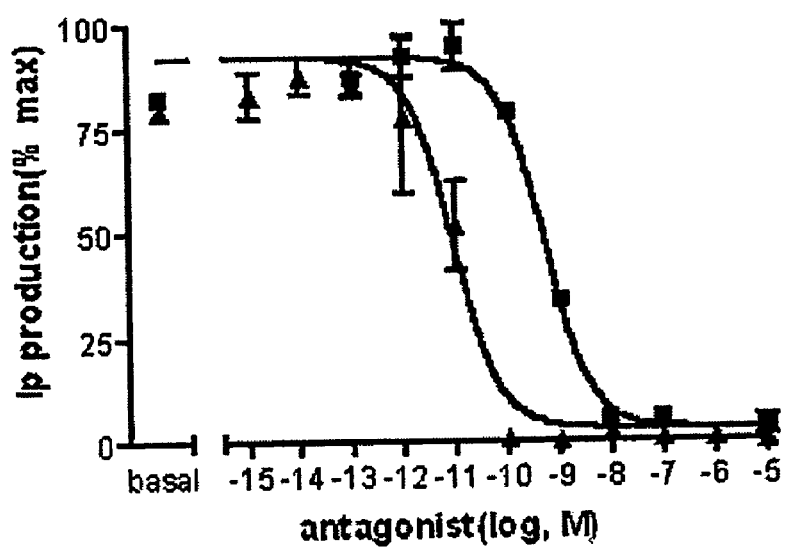
Figure 7:
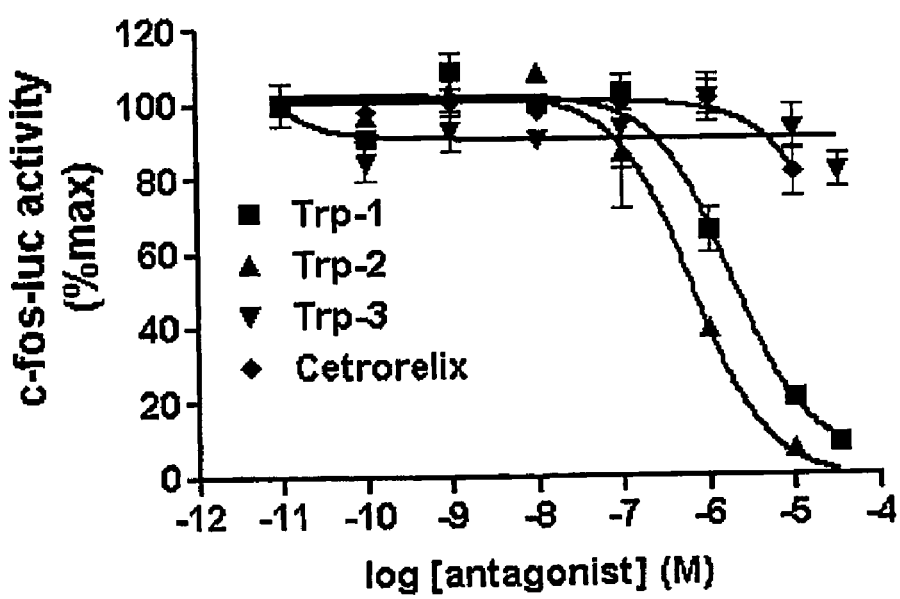
FIG. 7 is a graph showing the inhibition of GnRH-2-induced luciferase activity by treating Trptorelix-1, -2, and -3, which are GnRH-2 antagonists, and Cetrorelix, a GnRH-1 antagonist to cells expressing the GnRH-2 receptor that was found in Primates.

Trptorelix-1, which is an antagonist of GnRH-2, inhibits the production of IP induced by GnRH-2 in a concentration-dependent manner, and it shows about a 100 to 2800-fold higher inhibitory effect on bullfrog GnRH receptors than Cetrorelix, which is an agonist of GnRH-1 (FIG. 6a and FIG. 6b). On the other hand, Trptorelix-1 showed about a 60-fold lower effect on rat GnRH receptors than did Cetrorelix (FIG. 6c). Further, when cell lines expressing Primate GnRH-2 receptors were treated with Trptorelix-1 and Trptorelix-2, the activity of luciferase induced by GnRH-2 was reduced In a concentration-dependent manner, but treatment with Trptorelix-3 and Cetrorelix showed no effect (FIG. 7). It was revealed that, by substituting Leu and Arg which are the 7$^{th}$ and 8$^{th}$ amino acids of Cetrorelix, with Trp and Tyr, Trptorelix showed a high binding affinity with regard to GnRH-2 receptors whereas it showed a low binding affinity with regard to GnRH-1 receptors. Such a result shows that Trptorelix can effectively bind to GnRH-2 receptors and thereby inhibit their signal transduction. In summary, it is concluded that Trptorelix is a very specific antagonist for GnRH-2.

Figure 8A:
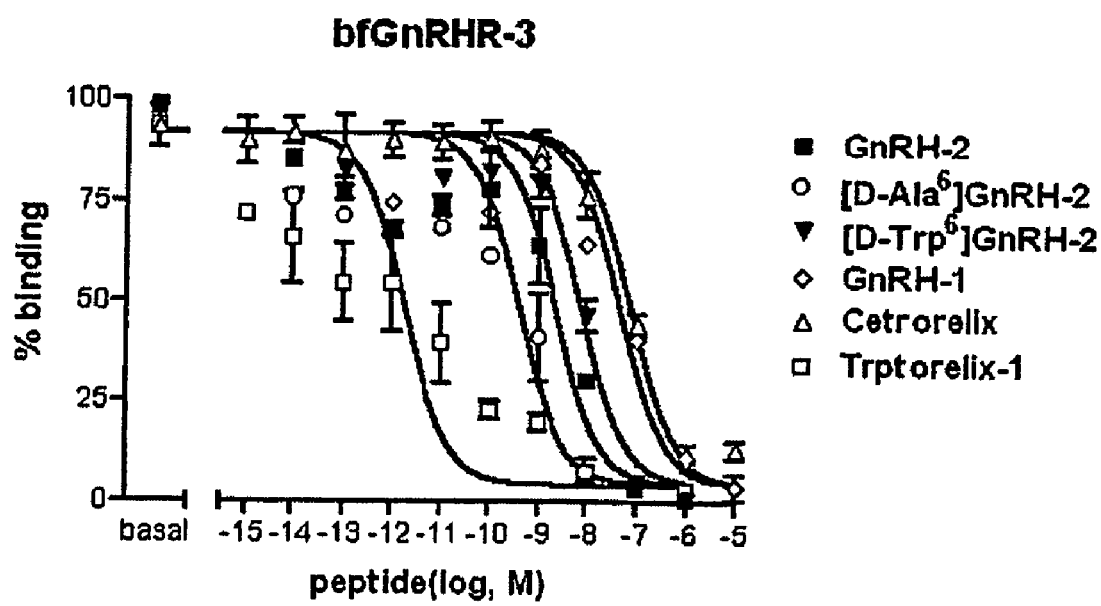
FIG. 8a and 8b are graphs showing binding abilities between GnRH-1, Cetrorelix, GnRH-2, Trptorelix-1, and GnRH-2 agonists, and receptors in each cell line expressing bullfrog GnRH-2 receptor and rat GnRH receptor.
Figure 8B:
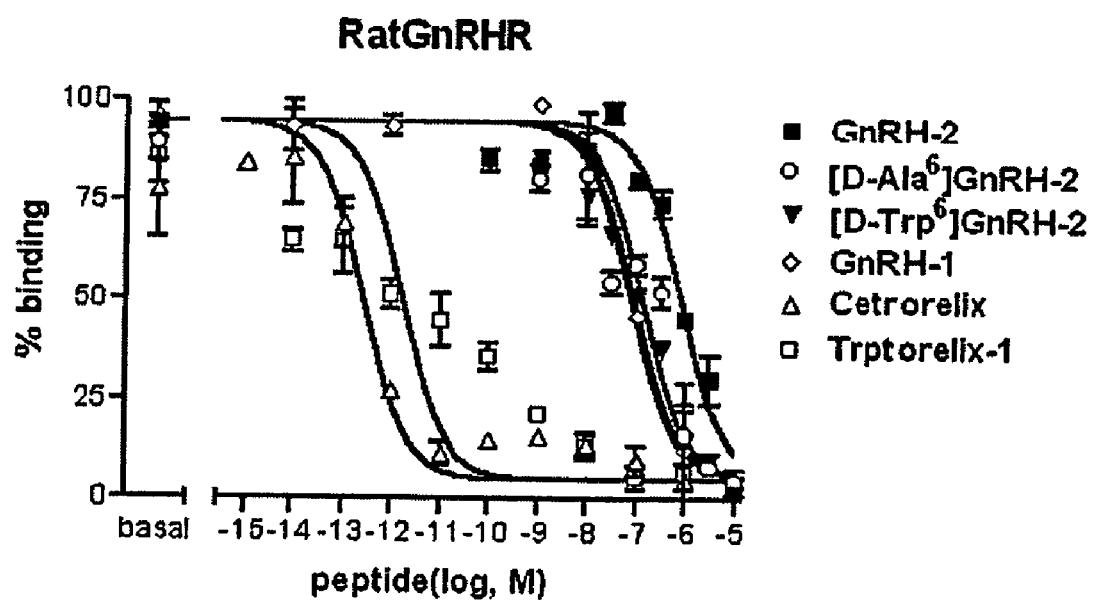

The relative binding affinity of the agonists and antagonists toward the receptors was determined, and as a result, the order of Trptorelix-1>[D-Ala$^6$]GnRH-2>GnRH-2>>[D-Ala$^6$]GnRH-2>GnRH-1>Cetrorelix with regard to the bfGnRH receptor was shown, and the order of Cetrorelix>Trptorelix-1>GnRH-1>[D-Ala$^6$]GnRH-2>[D-Trp$^6$]GnRH-2>GnRH-2 with regard to the rat GnRH receptor was shown (FIGS. 8a and 8b). These results also show that [D-Ala$^6$]GnRH-2 and Trptorelix-1 are an agonist and an antagonist specific to GnRH-2.

Also, [D-Arg$^6$]GnRH-2, [D-leu$^6$]GnRH-2, [D-Trp$^6$]GnRH-2, and [D-t-bu-Ser$^6$]GnRH-2, etc. described in PCT Laid-Open Publication No. 01-74377 were subjected to experiments in cell lines having receptors sensitive to GnRH-1, but they were not studied with regard to receptors sensitive to GnRH-2. That is, the effect of these analogs on GnRH-2 receptors was not verified. Particularly, the experiments conducted with [D-Trp$^6$]GnRH-2 by the inventors revealed that [D-Trp$^6$]GnRH-2 did not have a significantly better effect than did a wild-type ligand, whereas [D-Ala$^6$]GnRH-2 or [D-Lys$^6$]GnRH-2 developed in the invention had excellent efficiency with regard to GnRH-2 receptors as compared with the wild type ligand.

The present invention also relates to pharmaceutical compositions for regulating the release of gonadotropin comprising the agonists or antagonists regulating the activity of GnRH-2 by specifically binding to the GnRH-2 receptors, and pharmacologically acceptable carriers.

The agonists and antagonists for GnRH-2 can be used for the treatment of human reproductive physiological diseases and steroid-related cancer cells, and they can also be used in the raising industry of non-mammalian animals, i.e., birds and fish. Accordingly, the GnRH-2 agonists and antagonists can be employed for the prevention and treatment of diseases associated with the activity of GnRH-2 by regulating the activity of GnRH-2.

The pharmaceutical compositions comprising the GnRH-2 agonists or antagonists can be suitably selected according to the purpose of use, the type of the GnRH-2 analogs to be used, the physical condition of subjects, and administration methods and forms. For example, the content of the active ingredient of the pharmaceutical compositions may be prepared within the concentration of 0.1 nM-100 nM. The administration methods of the pharmaceutical compositions can be suitably selected by a person having ordinary knowledge in the art to which the invention pertains, and for example, oral administration or parenteral administration can be employed. In an embodiment of the present invention, when the pharmaceutical compositions are prepared so that the content of the active ingredient can be at the concentration of 0.1 nM-100 nM and then they are administered Into humans by injection, the amount by weight is about 0.1-100 μg/kg. Actually, in the invention, when a 100 g rat was treated with 10 μg of [D-Ala$^6$]GnRH-2, it was observed that the concentration of luteinizing hormone and testosterone in blood was increased in vivo (FIG. 4). In an embodiment of the present invention, the GnRH-2 antagonists and agonists were first synthesized, and then after moisture was completely eliminated there from by cooling and concentrating them, they were stored in glass bottles in a vacuum state. In the case of the agonists, they can be easily dissolved in distilled water, and the pharmaceutical compositions comprising them can be prepared by diluting them in saline. In the case of antagonists, they can be prepared by dissolving them in DMSO (dimethyl sulfoxide) or diluting them with saline.

The GnRH-2 analogs can be used for treating steroid-related diseases (ex: prostate cancer, breast cancer, and ovarian cancer, etc.), diseases associated with the hypofunction of reproductive endocrinology (ex: irregular menstruation, amenorrhea, precocious puberty, and hypogonadism), the control of ovulation periods in in vitro fertilization (ex: the ovulation periods can be optionally controlled by administering GnRH agonists or antagonists), contraception (ex: the growth of an embryo and implantation rate can be lowered by the administration of GnRH antagonists after sexual intercourse), increased production of fish and domestic animals, etc.

In connection with the molecular biological study of GnRH-2 receptors and the assay of physiological functions of GnRH-2, all of the GnRH receptors of non-mammals and the GnRH-2 receptor that has been found in monkeys are more sensitive to GnRH-2 than GnRH-1 (Wang et al., ibid.; Neill et al., ibid.). Accordingly, the GnRH-2 agonists and antagonists can be utilized for molecular biological study of these receptors, i.e., the binding affinity of ligand-receptors and molecular study of signal transduction mechanisms in cells. Further, although GnRH-2 is found in humans and other mammals, its functions have not been known (White et al., ibid.). Hence, the GnRH-2 agonists and antagonists can be used to study the physiological functions of GnRH-2.

For the treatment of breast cancer, prostate cancer, and ovarian cancer cells generated by steroids, GnRH-1 has been used (Schally, ibid. 1999; Grundker et al., ibid.). The agonists and antagonists of GnRH-1 have functions in regulating the secretion of steroids in the gonads, and thus, based on these functions, they have been used for the treatment of the cancers that are formed in prostate, breast, and ovary cells, as well as cancer cells. That is, all of the strong agonists and antagonists of GnRH-2 inhibit the secretion of steroids in testes, and thereby the concentration of steroids in the body becomes low, ultimately causing the inhibition of the proliferation of cancer cells.

Recent studies have revealed that GnRH receptors are expressed in these cancer cells, and thus studies about the direct effects of GnRH are now in progress. In these cancer cells, GnRH-1 exhibited more effectively than GnRH-2. In other words, GnRH-2 inhibited the proliferation of cancer cells at a lower concentration than that of GnRH-1 (Grundker et al., ibid.). Moreover, the inventors also proved that GnRH-2 bound more effectively to TSU-Pri cells, which are prostate cancer cells (FIG. 5). Therefore, when the analogs of GnRH-2 are used, they will inhibit the proliferation of cancer cells with a much lower cost because they can be treated at a lower concentration than that of the wild-type GnRH-2. Consequently, it is proposed that the agonists and antagonists of GnRH-2 will be very effective for the treatment of steroid-related cancer cells.

The agonists and antagonists of GnRH-2 can be used for the treatment of reproductive endocrine diseases. Recent studies have revealed that, like GnRH-1, GnRH-2 promoted the secretion of LH and FSH in the gonadal cells of the pituitary gland (Millar et al., ibid.; Padmanabhan and McNeily, 2001). While GnRH-1 is more effective for the secretion of LH, GnRH-2 is more effective for the secretion of FSH. FSH and LH have functions different from each other in reproductive endocrinology. For example, FSH promotes the growth of follicles in ovaries, and LH helps the release of ova from the matured follicles. It has been revealed that the secretion function of FSH by GnRH-2 is stronger than the LH secretion function by GnRH-1. These studies suggest that the GnRH-2 agonists and antagonists can be used to regulate the secretion of FSH and LH. The GnRH-1 has been used In hypogonadism, precocious puberty, irregular menstruation, etc. thus far (Huirne and Lambalk, 2001). However, both GnRH-1 and GnRH-2 promote the secretion of LH and FSH, but as they have different characteristics in that the GnRH-1 promotes the secretion of LH more effectively whereas the GnRH-2 promotes the secretion of FSH more effectively, the mixed use of the GnRH-1 and GnRH-2 analogs will exhibit much better efficacy. Consequently, the agonists and antagonists of GnRH-2 are expected to be able to be used for the treatment of such reproductive endocrinology system diseases.

The agonists and antagonists of GnRH-2 can be used in in vitro fertilization. In infertility patients, in vitro fertilization is a very important tool for pregnancy. For this purpose, the agonists and antagonists of GnRH are used in the control of ovulation periods. Likewise, the agonists and antagonists of GnRH-2 will be able to be used for the control of ovulation periods.

Also, the agonists and antagonists of GnRH-2 can be used for contraception. The GnRH and GnRH receptors are expressed at the early embryo development stage. Particularly, when the GnRH was treated at the early embryo development stage, the development of the embryo and implantation were enhanced, whereas when the GnRH antagonists are used, the development of the embryo and implantation were inhibited (Raga F, et al., Endocrinology vol.140 pp. 3705-3712, 1999). Therefore, the agonists and antagonists of GnRH-2 will be able to be used for contraception.

The agonists and antagonists of GnRH-2 can be used for the increased production of fish and domestic animals. The GnRH receptors that have been found in fish and birds thus far are more sensitive to GnRH-2 than GnRH-1. For overovulation of fish, GnRH-1 analogs have been used but their effects are insignificant. Consequently, [D-Ala$^6$]GnRH-2 and Trptorelix, which act on the receptors that are sensitive to GnRH-2, can be used for the increased production of fish and birds.

The present invention will be further described in more detail with reference to the following examples. The following examples are provided solely to illustrate the invention: the protection scope of the present invention should not be construed to be limited thereto.

EXAMPLES

Example 1

Construction of GnRH-2 Analogs

To develop agonists of GnRH-2, [D-Ala$^6$]GnRH-2 in which Gly, the 6$^{th}$ amino acid of GnRH-2, is substituted with D-Ala was constructed, and its sequence is shown in FIG. 1 and SEQ ID NO: 3. Also, [D-Ala$^6$]GnRH-2 in which Gly at the 6$^{th}$ position of GnRH-2 is substituted with D-Trp was designed. The GnRH-2 was purchased from Sigma Co. (US), and its amino acid sequence is shown in SEQ ID NO: 1.

Cetrorelix (Ac-D-2Nal-(4Cl)-D-Phe-D-3Pal-Ser-Tyr-D-Cit-Leu-Arg-Pro-D-Ala-NH$_2$), an antagonist of GnRH-1, was purchased from Serono Co. (Switzerland). Antagonists of GnRH-2 were constructed by substituting Tyr, Leu, and Arg, which are the 5$^{th}$, 7$^{th}$, and 8$^{th}$ amino acids of Cetrorelix with His, Trp, and Tyr, and they were named Trptorelix-1, Trptorelix-2, and Trptorelix-3. They are shown in SEQ ID NOS: 10 to 12.

[D-Ala$^6$]GnRH-2, [D-Trp$^6$]GnRH-2, and Trptorelix were constructed by chemical synthesis by AnyGen Co. (located in Kwangju Institute of Science and Technology, Kwangju, Republic of Korea).

Example 2

GnRH-2 Agonist-Induced GnRH-2 Receptor Activation

The GnRH receptor, a membrane protein connected with the G protein, activates the G protein when activated by aligand, and the activated G protein activates phospholipase C and thereby the synthesis of inositol phosphate (IP), which is the second transmitter in cells, is increased. Based on this principle, the activity of a receptor can be investigated by measuring the amount of IP within cells.

2-1 Inositol Phosphate Assay

GH3 cell lines were obtained from the Cell Line Bank at the Cancer Research Center, Seoul National University College of Medicine, located in Seoul, Republic of Korea. The GH3 cell lines were infected with retroviruses comprising genes encoding bfGnRHR-1, bfGnRHR-2, and bfGnRHR-3 which are bullfrog GnRH receptors, and rat GnRHR, and cell lines expressing each of these receptors were obtained. The GH3 cells expressing bfGnRHR-1, bfGnRHR-2, bfGnRHR-3, and rat GnRHR were cultured on 12-well plates. After 24 hours, the cells were cultured again for 24 hours in a media containing no inositol, to which $H^3$-myoinositol was added. The resultant cells were washed with buffer A (140 mM NaCl, 20 mM HEPES, 4 mM KCl, 8 mM D-Glucose, 1 mM $MgCl_2$, 1 mM $CaCl_2$, 1 mg/ml BSA) and then cultured in buffer A containing 10 mM LiCl at 37°C. for 30 minutes. Thereafter, they were treated with GnRH having a suitable concentration, cultured at 37° C. for another 30 minutes, and then the media was eliminated. The cells were treated with 10 mM of ice-cold formic acid to terminate the reaction, and the cell extracts were mixed with Dowex anionic exchange resins. These resins were washed with distilled water, IP was extracted with 1 M ammonium formate/0.1 M formic acid, and cpm (count per minute) was determined.

2-2: IP Production Induced by GnRH-2 Agonist

The GH3 cell lines were infected with retroviruses comprising genes encoding bfGnRHR-1, bfGnRHR-2, and bfGnRHR-3 which are bullfrog GnRH receptors, and rat GnRHR, and cell lines expressing each of these receptors were obtained. These cell lines were treated with GnRH-1, GnRH-2, and their agonists, and after 30 minutes, the formation of IP, which is the second signal transmitter, was investigated. In all the cell lines it was observed that when they were treated with GnRH and the agonists, IP was formed in a concentration-dependent manner. It was observed that with regard to all the bfGnRHR, GnRH-2 reacted more sensitively than GnRH-1, and with regard to the rat GnRH receptor, GnRH-1 reacted more sensitively than GnRH-2 (FIG. 2a to FIG. 2d, and Table 1).

These results agree with those that were already revealed, and they confirm that the non-mammalian GnRH receptors sensitively react to GnRH-2, and the mammalian GnRH receptor sensitively reacts to GnRH-1 (Neill et al., ibid.; Millar et al., ibid.; Wang et al., ibid.). As can be seen from FIG. 2a to FIG. 2d, when the GH3 cells expressing bfGnRHR-1 were treated with [D-Ala$^6$]GnRH-2 and [D-Trp$^6$]GnRH-2, which are agonists of GnRH-2, [D-Ala$^6$]GnRH-2 activated bfGnRHR-1 at about an 8-fold lower concentration than GnRH-2, and [D-Trp$^6$]GnRH-2 activated bfGnRHR-1 at a concentration similar to that of GnRH-2. When the GH3 cells expressing bfGnRHR-2 were treated with GnRH-1, GnRH-2, [D-Ala$^6$]GnRH-2, and [D-Trp$^6$]GnRH-2, [D-Ala$^6$]GnRH-2 acted on the receptor most sensitively and thereby induced the production of IP. GnRH-1 could activate bfGnRHR-2 at about a 1000-fold higher concentration than GnRH-2. Moreover, it was observed that in the cell lines expressing bfGnRHR-3, [D-Ala$^6$]GnRH-2 reacted most sensitively. On the other hand, in the cells expressing the rat GnRH receptor (rat GnRHR), GnRH-1 induced the production of IP most sensitively and [D-Ala$^6$]GnRH-2 and GnRH-2 showed a sensitivity lower than 10-fold.

TABLE 1

Log $EC_{50}$ Value for Each Receptor of GnRH

|  | GnRH-2 | [D-Ala$^6$]GnRH-2 | [D-Trp$^6$]GnRH-2 | GnRH-1 |
| --- | --- | --- | --- | --- |
| bfGnRHR-1 | −9.41 ± 0.13 | −9.91 ± 0.13 | −9.40 ± 0.12 | −8.52 ± 0.14 |
| bfGnRHR-2 | −8.98 ± 0.14 | −9.91 ± 0.19 | −9.21 ± 0.13 | −5.59 ± 0.14 |
| bfGnRHR-3 | −9.51 ± 0.10 | −9.89 ± 0.10 | −9.22 ± 0.11 | −8.42 ± 0.07 |
| ratGnRHR | −8.06 ± 0.13 | −8.49 ± 0.14 | −7.92 ± 0.12 | −9.69 ± 0.14 |

The above Table 1 shows the $EC_{50}$ value, the concentration inducing half-maximal stimulation of each receptor. The results as shown above exhibit that [D-Ala$^6$]GnRH-2 very sensitively acts on bfGnRHR-1, bfGnRHR-2 and bfGnRHR-3, which are receptors that are sensitive to GnRH-2, whereas its sensitivity drops with regard to rat GnRHR, which is sensitive to GnRH-1, and hence it is verified that [D-Ala$^6$]GnRH-2 is an agonist specific to GnRH-2.

2-3: Luciferase Activity Assay

Complimentary DNA (cDNA) for a Primate GnRH-2 receptor was obtained from a CV-1 cell genome. A nucleotide sequence assay revealed that it showed three nucleotide differences from the Primate GnRH-2 receptor that was already known (Neill et al., ibid.), and differences in two amino acids were also found. Plasmids having Primate GnRH-2 receptors where transfected into CV-1 cells. To assay the activity of the receptor, c-fos-luc where a luciferase gene is fused with a c-fos promoter was co-transfected as a probe gene. After 48 hours from transfection, the cells were treated with GnRH-2 agonists and then the activity of luciferase was assayed (Seong et al., Endocrinology vol 144 2003, 454-466).

2-4: GnRH-2 Agonist-induced Luciferase Activation

The injection of several GnRH-2 agonists into cells expressing Primate GnRH-2 receptors revealed that they all increased the activation of luciferase in a concentration-dependant manner. Of the GnRH-2 receptors, [D-Ala⁶]GnRH-2 performed excellently, showing effects about 3 times that of a wild-type ligand, GnRH-2. In the case of [D-Lys⁶]GnRH-2 and [D-Trp⁶]GnRH-2, however, it was revealed that their effects were rather reduced to about 1.5-fold and 1.2-fold, respectively, as compared with GnRH-2 (FIG. 3a and Table 2). On the other hand, [D-Ala⁶]GnRH-1, which is the agonist of GnRH-1, showed very low sensitivity as compared with GnRH-2. Accordingly, these results suggest that [D-Ala⁶]GnRH-2 is the most effective agonist for the GnRH-2 receptors that are found in Primates and non-mammals. When analogs where the $5^{th}$, $7^{th}$, and $8^{th}$ amino acids of [D-Ala⁶]GnRH-2 are substituted were used, it was observed that their effects were weaker than [D-Ala⁶]GnRH-2, and therefore it can be seen that it is important to maintain His, Trp, and Tyr that are found at the $5^{th}$, $7^{th}$, and $8^{th}$ positions of GnRH-2 as they are (FIG. 3b).

TABLE 2

Luciferase Activation by GnRH-2 Agonists in Cells Expressing Primate GnRH-2 Receptor

| GnRH analogues | Log $EC_{50}$ | Ratio$^a$ | $E_{max}$ (fold-induction) |
|---|---|---|---|
| GnRH-1 | −5.74 ± 0.15 | 446.68 | 12.87 ± 1.12 |
| GnRH-2 | −8.39 ± 0.10 | 1 | 11.74 ± 0.31 |
| [D-Ala⁶]GnRH-1 | −6.38 ± 0.10 | 102.33 | 8.91 ± 0.39 |
| [D-Ala⁶]GnRH-2 | −8.81 ± 0.12 | 0.38 | 11.84 ± 0.47 |
| [D-Lys⁶]GnRH-2 | −8.57 ± 0.11 | 0.66 | 11.74 ± 0.43 |
| [D-Trp⁶]GnRH-2 | −8.31 ± 0.09 | 1.20 | 11.20 ± 0.32 |
| [D-Ala⁶, Leu⁷]GnRH-2 | −7.95 ± 0.10 | 2.51 | 9.04 ± 0.27 |
| [Leu⁵, D-Ala⁶]GnRH-2 | −7.35 ± 0.12 | 10.96 | 6.22 ± 0.25 |
| [D-Ala⁶, Tyr⁷, Trp⁸]GnRH-2 | −7.57 ± 0.13 | 6.61 | 12.83 ± 0.56 |
| [Tyr⁵, D-Ala⁶, Leu⁸]GnRH-2 | −7.90 ± 0.24 | 3.01 | 7.35 ± 0.51 |

Log $EC_{50}$ values and $E_{max}$ values of GnRH-2 agonists are average values of experiments that were conducted independently three times. Ratio$^a$ represents the ratio of $EC_{50}$ values of other GnRH analogs based on $EC_{50}$ values of GnRH-2.

Example 3

GnRH-2 Agonist-Induced LH and Testosterone Secretion

Example 3: GnRH-2 Agonist-induced serum LH and testosterone levels [D-Ala⁶]GnRH-2 was dissolved in saline at a concentration of 100 μg/ml, and then 10 μg of [D-Ala⁶]GnRH-2 was injected into the cervix of a male rat (Sprague Dawley rat having a weight of approximately 100 g). 1, 2, 4, and 8 hours after the injection, serum was obtained from the rat. The concentration of luteinizing hormone and testosterone present in the serum was measured by radioimmunoassay. When [D-Ala⁶]GnRH-2 was injected into the male rat, an increase of luteinizing hormone (LH) was observed in only one hour. This effect, however, was rapidly reduced by 2 hours from the injection. On the other hand, testosterone, which is a male hormone, began to rapidly increase from 2 hours after the injection, it arrived at a peak point in 4 hours, and it exhibited a significantly high value even after 8 hours as compared with before the injection (FIG. 4).

Example 4

Presence of GnRH-2 Receptor in Prostate Cancer Cells

To characterize the presence of GnRH-2 receptors in prostate cancer cells, GnRH-1 and GnRH-2 were radiolabeled with $I^{125}$. TSU-Pri, which is one of the prostate cancer cell lines, was cultured along with the radiolabeled $I^{125}$GnRH-1 and $I^{125}$GnRH-2. As controls, the cells expressing rat GnRH receptors that readily bind to GnRH-1 and the cells expressing bfGnRHR-3 receptors that readily bind to GnRH-2 were used. The radiolabeled GnRH and the cells were cultured at room temperature for 6 hours, and then washed with PBS (phosphate-buffered saline) several times to eliminate the unbound GnRH. Thereafter, the cells were isolated and radioactivity from the cells was measured using a γ-counter. $I^{152}$GnRH-1 bound to the cells expressing rat GnRH receptors fairly well, and its binding was reduced when unradiolabeled GnRH-1 or GnRH-2 was treated as a competitor. On the other hand, when TSU-Pri cells, which are prostate cancer cells, were treated with $I^{152}$-radiolabeled GnRH-1, no binding with cells was observed (FIG. 5a). When TSU-Pri was treated with $I^{152}$GnRH-2, binding with cells was observed. In the latter case, when unradiolabeled GnRH-2 was used as a competitor, the binding was reduced but when unradiolabeled GnRH-1 was used as a competitor, the binding was not reduced (FIG. 5b). Moreover, when unradiolabeled GnRH-2 or GnRH-2 agonists were used as competitors at several concentrations, it was observed that the binding was reduced in a concentration-dependent manner (FIG. 5c). These results show that a receptor for GnRH-2 is present in prostate cancer cells, and suggest that [D-Ala⁶]GnRH-2 can be used for the treatment of prostate cancer.

Example 5

Effect of GnRH-2 Antagonists 5-1: Effect of GnRH-2 Antagonists on Non-Mammalian GnRH Receptor When each GH3 cell expressing bfGnRHR-2 and bfGnRHR-3 constructed in 2-2 above was treated with Trptorelix-1, which is the GnRH-2 antagonist, production of IP was not observed. However, Trptorelix-1 could reduce the production of IP induced by 1 nM GnRH-2, in a concentration-dependent manner (FIG. 6a to FIG. 6c). Such effect was revealed to be 100-fold more sensitive with regard to bfGnRHR-2 and about 1000-fold more sensitive with regard to bfGnRHR-3, than when treated with Cetrorelix, which is the antagonist of GnRH-1 (FIG. 3)

TABLE 3

Log IC$_{50}$ Value for Each Receptor of GnRH Antagonist

|  | Trptorelix-1 | cetrorelix |
|---|---|---|
| bfGnRHR-2 | −8.10 ± 0.08 | −6.43 ± 0.11 |
| bfGnRHR-3 | −8.49 ± 0.11 | −6.28 ± 0.13 |
| ratGnRHR | −9.27 ± 0.07 | −11.03 ± 0.12 |

On the other hand, Trptorelix-1 inhibited the activity of rat GnRHR induced by GnRH-1 but it was shown that its sensitivity was very low as compared with Cetrorelix, which is the antagonist of GnRH-1 (FIG. 6). Such a result suggests that Trptorelix specifically acts on bfGnRHR-3 sensitive to GnRH-2 whereas its efficiency for the rat GnRHR sensitive to GnRH-1 is lower than that of GnRH-1 antagonists. Table 3 shows the concentration (IC$_{50}$) of antagonists inducing half-maximal inhibition of GnRH receptor activity.

5-2: Effect of GnRH-2 Antagonists on Primate GnRH-2 Receptor

In the same manner as in 2-3 above, Primate GnRH-2 receptors were co-transfected along with c-fos-luc reporter genes, and after 48 hours, GnRH-2 and GnRH-2 antagonists were treated thereinto at the same time and then the effect of GnRH-2 antagonists was observed. When the cell line expressing the Primate GnRH-2 receptor was treated with Trptorelix-1 and Trptorelix-2, the activity of luciferase induced by GnRH-2 was reduced in a concentration-dependent manner, but Trptorelix-3 and Cetrorelix showed no effect (FIG. 7 and Table 4). This shows that by substituting Leu and Arg, which are the 7$^{th}$ and 8$^{th}$ amino acids of Cetrorelix, with Trp and Tyr, Trptorelix showed a high binding affinity with regard to GnRH-2 receptors whereas it showed low binding affinity with regard to GnRH-1 receptors. Such result shows that Trptorelix can effectively bind to GnRH-2 receptors and thereby inhibit their signal transduction.

TABLE 4

Log IC$_{50}$ Value for Each Receptor of GnRH Antagonists.

| Reporter | antagonist | Log IC$_{50}$ |
|---|---|---|
| c-fos-luc | Trp-1 | −5.74 ± 0.10 |
|  | Trp-2 | −6.19 ± 0.12 |
|  | Trp-3 | ND$^a$ |
|  | Cetrorelix | ND$^a$ |

Log IC$_{50}$ value by antagonists is an average value of experiments that were conducted independently three times. ND stands for "not detected" which means that there are no inhibitory functions.

Example 6

Ligand-Receptor Binding Assay 6-1

To determine the binding affinity between GnRH and GnRH receptors, GnRH-2 was radiolabeled with I$^{125}$. The GH3 cells expressing bfGnRHR-1, bfGnRHR-2, bfGnRHR-3, and rat GnRHR constructed in Example 2-3 above were cultured on 100-mm dishes. After 48 hours, the cells were homogenized to obtain cellular membranes, which were then dissolved in binding buffer (40 mM Tris, pH 7.4, 2 mM MgCl$_2$). 20 μg of membrane proteins were reacted with I$^{125}$-GnRH-2 at 4° C. for 16 hours. To this were added unradiolabeled GnRH-1, GnRH-2, [D-Ala$^6$]GnRH-2, [D-Trp$^6$]GnRH-2, and Trptorelix-1, which were then reacted along with I$^{125}$-GnRH-2 to investigate their binding affinity toward the receptors. Non-specific binding affinity was obtained from the competitive reaction with 100 μM of GnRH-2. After the reaction was completed, 1$^{125}$-GnRH-2 bound to the receptors was filtered using a Brandel harvester, and cpm was measured using a γ-counter.

6-2: Binding Affinity of GnRH-2 Agonists and Antagonists toward Receptors

The GH3 cells expressing bfGnRHR-3 obtained from Example 6-1 above were treated with 1$^{125}$GnRH-2 and GnRH-2 agonists and antagonists at various concentrations to determine the binding affinity of GnRH-2 agonists and antagonists toward the receptors. With regard to bfGnRHR, the binding affinity was shown in the order of Trptorelix-1>[D-Ala$^6$]GnRH-2>GnRH-2>[D-Trp$^6$]GnRH-2>GnRH-1>Cetrorelix, and with regard to rat GnRHR, it was in the order of Cetrorelix>Trptorelix-1>GnRH-1>[D-Ala$^6$]GnRH-2>[D-Trp$^6$]GnRH-2>GnRH-2 (FIG. 4a to FIG. 4b, and Table 5). These results suggest that Trptorelix binds to bfGnRHR-3 more effectively than GnRH-2.

TABLE 5

Binding Affinity of GnRH Agonists and Antagonists toward Receptors (log IC$_{50}$ Value)

|  | GnRH-2 | [D-Ala$^6$]GnRH-2 | [D-Trp$^6$]GnRH-2 | GnRH-1 | Cetrorelix | Trptorelix-1 |
|---|---|---|---|---|---|---|
| bfGnRHR-3 | −8.63 ± 0.14 | −9.83 ± 0.14 | −8.10 ± 0.11 | −7.32 ± 0.17 | −7.11 ± 0.08 | −11.73 ± 0.19 |
| ratGnRHR | −6.08 ± 0.08 | −6.85 ± 0.13 | −7.01 ± 0.09 | −7.08 ± 0.10 | −12.55 ± 0.15 | −11.75 ± 0.19 |

The present invention provides agonists and antagonists of gonadotropin-releasing hormone-2 (GnRH-2) which regulate the activity of GnRH-2 by specifically binding to GnRH-2 receptors, and pharmaceutical compositions comprising them. Advantages thereof include their usefulness for the treatment of reproductive physiology diseases and steroid-related cancer cells because they specifically bind to the GnRH-2 receptors and effectively regulate GnRH-2, and they are applicable to the raising industry of non-mammalian animals, i.e., birds and fish.

What is claimed is:

1. A peptide-based gonadotropin-releasing hormone-2 (GnRH-2) antagonist which inhibits the activity of GnRH-2 by specifically binding to a GnRH-2 receptor, comprising the following peptide (SEQ ID NO:9):

Ac-D-2Nal-(A)-D-Phe-D-3Pal-Ser-$Xaa_5$-D-Cit-Trp-$Xaa_8$-Pro-D-AlaNH$_2$; wherein A is 4Cl, 4F, or 4 Br;

$Xaa_5$ is Tyr or His; and $Xaa_8$ is Tyr or Leu.

2. The GnRH-2 antagonist of claim 1, wherein said antagonist is selected from the group consisting of peptides shown in SEQ ID NO:10 to SEQ ID NO:12.

3. A pharmaceutical composition for regulating the release of gonadotropin comprising the GnRH-2 antagonist according to claims 1 or 2 as an active ingredient, and a pharmaceutically acceptable carriers.

* * * * *